United States Patent
Coyle et al.

(10) Patent No.: US 9,196,455 B2
(45) Date of Patent: *Nov. 24, 2015

(54) ION BEAM SAMPLE PREPARATION APPARATUS AND METHODS

(71) Applicant: Gatan, Inc., Pleasanton, CA (US)

(72) Inventors: Steven Thomas Coyle, Alameda, CA (US); John Andrew Hunt, Fremont, CA (US); Michael Patrick Hassel-Shearer, Little Haseley (GB)

(73) Assignee: Gatan, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/341,842

(22) Filed: Jul. 27, 2014

(65) Prior Publication Data
US 2014/0332699 A1 Nov. 13, 2014

Related U.S. Application Data

(63) Continuation of application No. 13/949,318, filed on Jul. 24, 2013, now Pat. No. 8,791,438.

(60) Provisional application No. 61/676,368, filed on Jul. 27, 2012.

(51) Int. Cl.
| | |
|---|---|
| *H01J 37/00* | (2006.01) |
| *H01J 37/20* | (2006.01) |
| *G01N 1/32* | (2006.01) |
| *H01J 37/30* | (2006.01) |
| *H01J 37/305* | (2006.01) |
| *G01N 21/84* | (2006.01) |

(52) U.S. Cl.
CPC . *H01J 37/20* (2013.01); *G01N 1/32* (2013.01); *H01J 37/3005* (2013.01); *H01J 37/3056* (2013.01); *G01N 2021/8411* (2013.01); *H01J 2237/184* (2013.01); *H01J 2237/202* (2013.01); *H01J 2237/31745* (2013.01)

(58) Field of Classification Search
USPC .......................................... 250/492.3
See application file for complete search history.

(56) References Cited

U.S. PATENT DOCUMENTS

| | | |
|---|---|---|
| 4,272,682 A | 6/1981 | Swann |
| 5,472,566 A | 12/1995 | Swann et al. |
| 5,907,157 A | 5/1999 | Yoshioka et al. |
| 5,922,179 A | 7/1999 | Mitro et al. |
| 5,986,264 A | 11/1999 | Grunewald |
| 6,406,589 B1 | 6/2002 | Yanagisawa |
| 6,768,110 B2 | 7/2004 | Alani |
| 6,784,427 B1 | 8/2004 | Grunewald et al. |
| 6,914,244 B2 | 7/2005 | Alani |
| 7,354,500 B2 | 4/2008 | Yoshioka et al. |

(Continued)

*Primary Examiner* — Phillip A Johnston
(74) *Attorney, Agent, or Firm* — Theodore Heske, III

(57) ABSTRACT

Ion beam sample preparation apparatus and methods are described. The apparatus has disposed in a vacuum chamber at least one tilting ion beam irradiating means with intensity control, a rotation stage with rotation control, a sample holder, and an adjustable positioning stage that has two axes of positional adjustment that are operable to move the region of the sample being prepared by the ion beam relative to the ion beam. The apparatus may also include a vacuum-tight optical window for observing the sample and a shutter for protecting the optical window from debris while the sample is prepared in the ion beam. The apparatus may also include an instrument controller responsive to the state of the apparatus and to the condition of the sample and is operable to control the preparation of the sample.

22 Claims, 10 Drawing Sheets

(56) References Cited

U.S. PATENT DOCUMENTS

| | | | |
|---|---|---|---|
| 7,777,183 B2 * | 8/2010 | Kaneoka | G01N 23/225 250/306 |
| 7,968,843 B2 * | 6/2011 | Nishiyama | G01N 23/2204 250/306 |
| 8,227,781 B2 * | 7/2012 | Zaykova-Feldman | G01N 1/32 250/239 |
| 8,283,642 B2 | 10/2012 | Coyle et al. | |
| 8,384,050 B2 | 2/2013 | Coyle et al. | |
| 8,445,874 B2 | 5/2013 | Coyle et al. | |
| 8,497,487 B2 * | 7/2013 | Milas | H01J 37/20 250/440.11 |
| 8,791,438 B2 * | 7/2014 | Coyle et al. | 250/492.3 |
| 2002/0000522 A1 | 1/2002 | Alani | |
| 2005/0081997 A1 | 4/2005 | Yoshioka et al. | |
| 2005/0118065 A1 | 6/2005 | Hasegawa et al. | |
| 2006/0011868 A1 | 1/2006 | Kidron et al. | |
| 2006/0255295 A1 | 11/2006 | Yoshioka et al. | |
| 2007/0115468 A1 * | 5/2007 | Barnard | H01J 37/228 356/300 |
| 2008/0283748 A1 * | 11/2008 | Matsumoto | H01J 37/20 250/311 |

\* cited by examiner

ION BEAM SAMPLE PREPARATION APPARATUS AND METHODS

CROSS REFERENCE TO RELATED APPLICATIONS

This application is a continuation of prior filed non-provisional utility application Ser. No. 13/949,318 filed Jul. 24, 2013. Non-provisional utility application Ser. No. 13/949,318 claims the benefit of prior filed provisional Application No. 61/676,368 filed Jul. 27, 2012. Application Ser. No. 13/949,318 is incorporated herein by reference. Application No. 61/676,368 is incorporated herein by reference.

STATEMENT REGARDING FEDERALLY SPONSORED RESEARCH OR DEVELOPMENT

Not Applicable.

DESCRIPTION OF ATTACHED APPENDIX

Not Applicable.

BACKGROUND

The present disclosure relates to the use of one or more ion beams to prepare materials for microscopic observation or spectroscopic analysis. Microscopic observational techniques include, but are not limited to, optical microscopy, scanning electron microscopy (SEM), transmission electron microscopy (TEM), scanning transmission electron microscopy (STEM), and reflection electron microscopy (REM). Spectroscopic analysis techniques include, but are not limited to, x-ray micro-analysis, reflection electron energy-loss spectroscopy (REELS), electron back-scattered diffraction (EBSD), x-ray photoelectron spectroscopy (XPS), and Auger electron spectroscopy (AES). Materials to be viewed under any microscopic technique may require processing to produce a sample suitable for microscopic examination.

Transmission electron microscopy (TEM) is an important technique for studying the detailed microstructure of many materials. The preparation of samples for atomic resolution TEM is very demanding, requiring a final sample that is very thin (i.e. <50 nanometers) and free from artifacts. Typically, sample preparation involves initial slicing, sectioning, and mechanical thinning to produce a relatively thin (i.e. 100-200 micrometers) disk of sample material. Ion beam milling of the sample may then be employed to further thin, smooth, and expose regions of interest in the sample for later TEM study, typically producing a sample with a thickness of 50 nanometers.

Ion beam milling of a material can produce samples that are well suited for microscopic examination. An ion beam irradiating device may generate, accelerate, and direct a beam of ions toward a sample. The impact of ions on the sample will sputter material away from the area of ion impact. Furthermore, the sample surface may be polished by the ion beam to a substantially smooth condition, further enhancing observational properties of the sample. Regions of interest in the sample may be exposed and polished by the use of ion beams, thus making a suitable observational sample from the material under investigation.

Ion beam systems used to mill samples destined for TEM analysis typically expose an interface or produce a sample with an electron transparent region. Many of these systems have rotating samples and fixed beams, so that the beams may strike the sample from multiple directions. This provides for more uniform milling of a sample by compensating for the shadowing of certain regions that may happen due to the nonuniform topology of the sample surface. In the typical system used for ion beam milling, material is removed most quickly from the sample by the ion beam in the region of the sample described by the intersection of the rotation axis of the sample with the center of the ion beam itself. It is often difficult to position a sample in the ion beam system so that the specific region of interest lies at the center of rotation. Some amount of trial and error may be expected when trying to target a specific region of interest in the ion beam sample preparation process.

Important considerations to users of the ion beam milling technique include: reducing or minimizing the time and effort the user is occupied in processing the sample; reducing or minimizing the number of steps where delicate samples are directly handled and at risk for damage, such as during mounting to sample holders for processing or analysis; reducing or minimizing the time and effort the user is occupied transferring the sample into the ultimate analysis equipment (imaging or spectroscopy), and aligning the coordinates of the prepared sample region to the ultimate analysis equipment prior to analysis; ensuring high quality and high probability of success in processing and imaging the sample; reducing or minimizing the time that the ion milling equipment and sample mounting equipment are occupied for each sample; and ensuring high-quality microscopy observation of the sample during sample mounting and ultimate analysis by reducing the working distance required between the sample and the objective or probe-forming lens used for observation.

In consideration of the foregoing points, it is clear that embodiments of the present disclosure confer numerous advantages and are therefore highly desirable.

SUMMARY

The present disclosure is directed to ion beam sample preparation apparatus and methods for using the disclosed apparatus to prepare samples for later observation. Features of the disclosure enable adjustable multi-axis micro-positioning of a sample within the ion beam, thereby conferring numerous advantages in finding, spotting, and exposing a region of interest within the sample being prepared. Additional features of the disclosure provide benefits in: minimizing the handling of delicate samples, improving the diagnostic viewing of the sample undergoing preparation, and improving the overall efficiency of the ion beam sample preparation process. Additional features of the disclosure provide for instrumented control of the sample preparation apparatus using sample imaging.

An apparatus for preparing a sample using an ion beam according to an embodiment of the present disclosure comprises: a first ion beam irradiating means disposed in a vacuum chamber and directing a first ion beam toward said sample, said first ion beam irradiating means operatively coupled to a first ion beam intensity control means, said first ion beam having a first central ion beam axis, said first ion beam intensity control means operative to produce at least two different ion beam intensities; a first ion beam tilt control means operatively coupled to said first ion beam irradiating means and configured to provide at least two different tilt angles of said first ion beam irradiating means; a rotation stage disposed inside said vacuum chamber having a rotation axis and coupled to a rotation drive, said rotation drive operative to rotate said rotation stage around said rotation axis, said rotation axis being positioned to intersect a portion of said first ion beam; an adjustable positioning stage that is adjustably coupled to said rotation stage, said adjustable positioning stage comprising a sample holder retention means configured to releasably retain a sample holder, said sample holder comprising: a sample holder retained portion; at least one sample support arm configured to support said sample; and a sample holder bore that allows an unobstructed line-of-sight through the entirety of sample holder retained portion onto said sample being held by said one or more sample support arms; said sample holder further characterized as positioning said sample so that said rotation axis and said first central ion beam axis both intersect substantially the same portion of said sample that is being prepared in said first ion beam; said sample holder further characterized in that no portion of said sample support arm is intersected by said rotation axis while said sample is being prepared by said ion beam; said adjustable positioning stage further comprising: a first position adjustment means configured to move said adjustable positioning stage along a first adjustment axis; and, a second position adjustment means configured to move said adjustable positioning stage along a second adjustment axis; a vacuum-tight optically-transparent vacuum window disposed to permit direct, line-of-sight viewing from outside the vacuum chamber of at least a portion of said sample while said sample is being prepared in said first ion beam; and, a shutter means disposed between said vacuum window and said sample holder; said shutter means further characterized as having a shutter closed position in which said vacuum window is substantially sealed from the interior of said vacuum chamber, and, said shutter means further characterized as having a shutter open position that permits direct, line-of-sight viewing from outside the vacuum chamber of at least a portion of said sample while said sample is being prepared in said first ion beam; a first illumination source directing light through said sample holder bore toward said sample and further characterized in that at least a portion of the light emitted by said first illumination source strikes at least a portion of said sample while said sample is being prepared in said first ion beam; and, a sample viewing means having an optical axis directed toward the region where said first central ion beam axis substantially intersects said rotation axis, said sample viewing means further characterized as providing a magnified and substantially focused view of the region of said sample being prepared by said first ion beam.

In a related embodiment the first illumination source is further characterized as producing substantially monochromatic light. In another related embodiment the apparatus further comprises: a second illumination source directing light toward said sample and further characterized in that at least a portion of the light emitted by said second illumination source strikes at least a portion of said sample while said sample is being prepared in said first ion beam. In another related embodiment the apparatus further comprises: a sample imaging means that is operative to capture one or more images made available by said sample viewing means.

In another related embodiment the apparatus the sample imaging means is operative to save one or more previously captured images. In another related embodiment the is further characterized in that the sample imaging means is operative to save one or more unique indicia with each said one or more previously captured images. In another related embodiment of the apparatus the sample imaging means is operative to display said one or more previously captured images. In another related embodiment the apparatus is further characterized in that the sample imaging means is operative to receive said one or more unique indicia and display said one or more previously captured images corresponding with said one or more unique indicia. In another related embodiment the apparatus is further characterized in that the sample imaging means is operative to receive one or more annotations identifying the location one or more regions of interest within said one or more previously captured images and saving said one or more annotations with said one or more previously captured images.

An apparatus for preparing a sample using an ion beam according to an embodiment of the present disclosure comprises: a first ion beam irradiating means disposed in a vacuum chamber and directing a first ion beam toward said sample, said first ion beam irradiating means operatively coupled to a first ion beam intensity control means, said first ion beam having a first central ion beam axis, said first ion beam intensity control means operative to produce at least two different ion beam intensities; a first ion beam tilt control means operatively coupled to said first ion beam irradiating means and configured to provide at least two different tilt angles of said first ion beam irradiating means; a rotation stage disposed inside said vacuum chamber having a rotation axis and coupled to a rotation drive, said rotation drive operative to rotate said rotation stage around said rotation axis, said rotation axis being positioned to intersect a portion of said first ion beam; an adjustable positioning stage that is adjustably coupled to said rotation stage, said adjustable positioning stage comprising a sample holder retention means configured to releasably retain a sample holder, said sample holder comprising: a sample holder retained portion; at least one sample support arm configured to support said sample; and a sample holder bore that allows an unobstructed line-of-sight through the entirety of sample holder retained portion onto said sample being held by said one or more sample support arms; said sample holder further characterized as positioning said sample so that said rotation axis and said first central ion beam axis both intersect substantially the same portion of said sample that is being prepared in said first ion beam; said sample holder further characterized in that no portion of said sample support arm is intersected by said rotation axis while said sample is being prepared by said ion beam; said adjustable positioning stage further comprising: a first position adjustment means configured to move said adjustable positioning stage along a first adjustment axis; and, a second position adjustment means configured to move said adjustable positioning stage along a second adjustment axis; a vacuum-tight optically-transparent vacuum window disposed to permit direct, line-of-sight viewing from outside the vacuum chamber of at least a portion of said sample while said sample is being prepared in said first ion beam; and, a shutter means disposed between said vacuum window and said sample holder; said shutter means further characterized as having a shutter closed position in which said vacuum window is substantially sealed from the interior of said vacuum chamber, and, said shutter means further characterized as having a shutter open position that permits direct, line-of-sight viewing from outside the vacuum chamber of at least a portion of said sample while said sample is being prepared in said first ion beam; a first illumination source directing light toward said sample and further characterized in that at least a portion of the light emitted by said first illumination source strikes at least a portion of said sample while said sample is being prepared in said first ion beam; a sample viewing means having an optical axis directed toward the region where said first central ion beam axis substantially intersects said rotation axis, said sample viewing means further characterized as providing a magnified and substantially focused view of the region of said sample being prepared by said first ion beam; a sample imaging means that is operative to capture one or more images made available by said sample viewing means, said sample imaging means further characterized as being operatively coupled to a first communications channel and being responsive to said communications channel for capturing one or more images and communicating one or more captured images over said first communications channel; and, an instrument controller that is operative to: communicate with and control the actions of said sample imaging means through said first communications channel; communicate with and control the actions of a shutter actuation means through a second communications channel, said shutter actuation means being operative to move said shutter means between said shutter open position and said shutter closed position in response to communications received through said second communications channel.

In a related embodiment the apparatus is further characterized in that the instrument controller is operative to communicate with and control the actions of said first ion beam intensity control means through a third communications channel, the first ion beam intensity control means being operative to change the intensity of said first ion beam in response to communications received through said third communications channel. In another related embodiment the apparatus is further characterized in that the instrument controller is operative to communicate with and control the actions of said first ion beam tilt control means through a fourth communications channel, said first ion beam tilt control means being operative to change the intensity of said first ion beam in response to communications received through said fourth communications channel. The apparatus may be further characterized in that the instrument controller is operative to communicate with and control the actions of said rotation drive through a fifth communications channel, said rotation drive being operative to change the position of said rotation stage in response to communications received through said fifth communications channel.

In a related embodiment the apparatus is further characterized in that: the instrument controller is operative to communicate with and control the actions of said first ion beam intensity control means through a third communications channel, the first ion beam intensity control means being operative to change the intensity of said first ion beam in response to communications received through said third communications channel; the instrument controller is operative to communicate with and control the actions of said first ion beam tilt control means through a fourth communications channel, said first ion beam tilt control means being operative to change the intensity of said first ion beam in response to communications received through said fourth communications channel; and, the instrument controller is operative to communicate with and control the actions of said rotation drive through a fifth communications channel, said rotation drive being operative to change the position of said rotation stage in response to communications received through said fifth communications channel.

In a related embodiment the apparatus is further characterized in that the instrument controller is operative to extract one or more features from one or more captured images, and in response to one or more extracted features said instrument controller is operative to control at least one of the group consisting of said sample imaging means, said shutter actuation means, said first ion beam intensity control means, said first ion beam tilt control means, and said rotation drive. In another related embodiment the apparatus may be further characterized in that the instrument controller is operative to extract a feature from one or more captured images that indicates that said sample is perforated, said instrument controller being further characterized as being operative to respond to the extraction of said feature by causing said first ion beam intensity control means to change the ion beam intensity. In another related embodiment the apparatus may be further characterized in that the instrument controller is operative to extract a feature from one or more captured images that represents a stopping condition, and in response to extracting said stopping condition said instrument controller is operative to cease preparing said sample in said first ion beam.

In a related embodiment the apparatus is characterized in that the instrument controller is operative to extract a feature from one or more captured images that indicates that said sample is approaching perforation, said instrument controller being further characterized as being operative to respond to the extraction of said feature by causing said first ion beam intensity control means to change the intensity of said first ion beam. In another related embodiment the apparatus the apparatus may be further characterized in that the instrument controller is operative to: extract a feature from one or more captured images that is representative of one or more interference rings; and, extract a feature from one or more captured images that is representative of a change over time of said one or more interference rings; said instrument controller being further characterized as being operative to respond to the extraction of said features by causing said first ion beam intensity control means to change the intensity of said first ion beam. In another related embodiment the apparatus may be further characterized in that the rotation drive is operative to provide a rotation angle to the instrument controller, and the instrument controller is operative to capture an image and annotate said captured image with said rotation angle.

In a related embodiment the apparatus is characterized in that the rotation drive is operative to provide a rotation angle to the instrument controller, and the instrument controller is operative to capture one or more images at substantially the same rotation angle. In another related embodiment the apparatus may be further characterized in that the instrument controller is operative to use one or more acquisition parameters to control at least one from the group consisting of said sample imaging means, said shutter actuation means, said first ion beam intensity control means, and said first ion beam tilt control means; and, said rotation drive, when said shutter means is in said shutter closed position, and the apparatus is further characterized in that the instrument controller is operative to use one or more acquisition parameters to control at least one of the group consisting of said sample imaging means, said shutter actuation means, said first ion beam intensity control means, said first ion beam tilt control means, and said rotation drive, when said shutter means is in said shutter open position.

BRIEF DESCRIPTION OF THE DRAWINGS

These and other features, aspects, and advantages of the present invention will become better understood with regard to the following description, appended claims, and accompanying drawings where:

LIST OF REFERENCE NUMBERS APPEARING IN THE FIGURES

Figure 1:
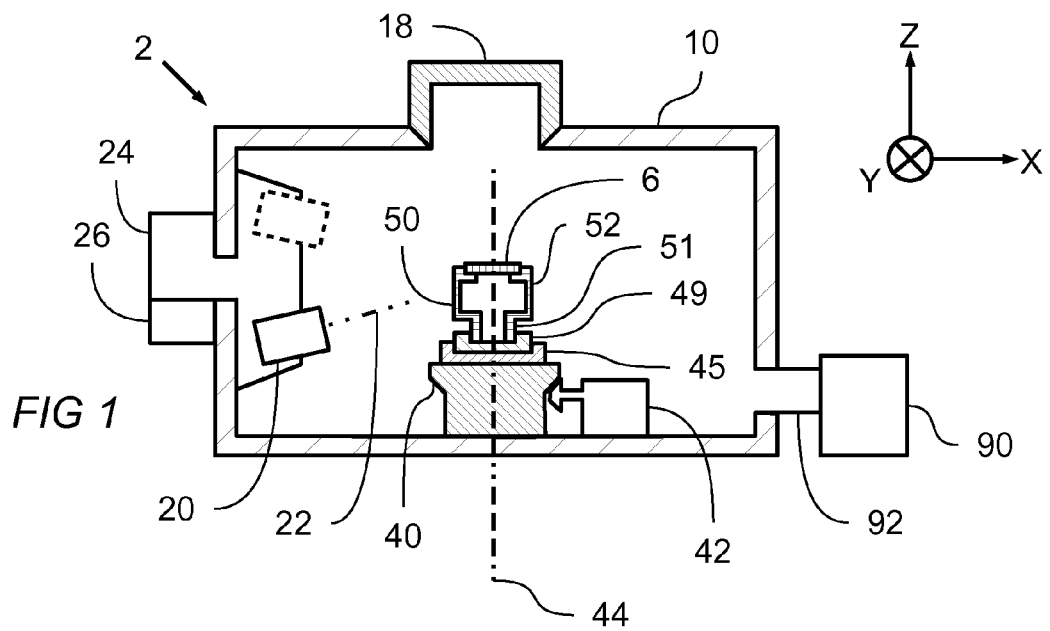
FIG. 1 shows schematic cross sectional view of an ion beam sample preparation apparatus according to the present disclosure.

2—ion beam sample preparation apparatus
6—sample
8—sample peripheral edge
9—sample surface
9a, 9b—first, second sample surface
10—vacuum chamber
16—loading chamber
18—chamber cover
20—ion beam irradiating means
20a, 20b—first, second ion beam irradiating means
22—central ion beam axis
22a, 22b—first, second central ion beam axis
24—ion beam intensity control means
24a, 24b—first, second ion beam intensity control means
26—ion beam tilt control means
26a, 26b—first, second ion beam tilt control means
40—rotation stage
42—rotation drive
44—rotation axis
45—adjustable positioning stage
46a, 46b—first, second adjustment axis
47—positioning stage cover
48a, 48b—first, second position adjustment means
49—sample holder retention means
50—sample holder
51—sample holder retained portion
52—sample support arm
52a, 52b—first, second sample support arm
54—sample holder bore
60—lighting source
60a, 60b—first, second illumination source
70—sample viewing window
71—sample viewing means
72—shutter means
73—shutter actuation means
74—sample imaging means
76—optical axis
80—rotation stage lifting means
86—raised position
88—processing position
90—vacuum pump means
92—pumping manifold
92a, 92b—first, second pumping manifold
100—instrument controller
102a, 102b, 102c, 102d, 102e—first, second, third, fourth, and fifth communications channel
200, 202, 204, 206, 208, 210, 212, 214, 216, 218—process steps
300, 302, 304, 306, 308, 310, 312, 314, 316—process steps
400, 402, 404, 406, 408, 410—process steps

DESCRIPTION

Embodiments of the present disclosure provide ion beam sample preparation apparatus and methods capable of producing a thin, polished, electron-transparent region from a sample. In particular, the present disclosure describes a multi-axis micro-positioning stage that improves the ability to view and process a region of interest in the sample. The disclosed improvement has the benefits of: minimizing sample handling; improving the ability to position a region of interest that is within the sample in the center of the ion beam, thereby improving processing efficiency; and, improving the ability to position the sample for diagnostic imaging while the sample is being prepared in the ion beam.

Turning now to FIG. 1, an embodiment of an ion beam sample preparation apparatus 2 according to the present disclosure is shown comprising: a vacuum chamber 10 in which a sample 6 is prepared; chamber cover 18 which seals vacuum chamber 10 from the outside atmosphere; vacuum pump means 90 and pumping manifold 92 which together bring vacuum chamber 10 to vacuum levels appropriate for ion beam milling; an ion beam irradiating means 20, which creates and directs an ion beam having a central ion beam axis 22 toward sample 6; an ion beam intensity control means 24, which is operative to provide at least two different ion beam intensities; an ion beam tilt control means 26, which is operative to provide at least two different tilt angles of ion beam irradiating means 20; a rotation stage 40 disposed inside vacuum chamber 10 having a rotation axis 44 and a rotation drive 42; an adjustable positioning stage 45 which is adjustably coupled to rotation stage 40, the adjustable positioning stage 45 comprising: a sample holder retention means 49 configured to releasably retain sample holder 50, the sample holder 50 comprising: a sample holder retained portion 51 and at least one sample support arm 52 by which sample 6 may be held; support arm 52 being further characterized as positioning sample 6 so that rotation axis 44 and central ion beam axis 22 both intersect substantially the same portion of sample 6 while the sample is being prepared in the ion beam, and no portion of sample support arm 52 is intersected by rotation axis 44 while the sample is being prepared in the ion beam. When in the retained position, sample holder 50 locates sample 6 in a predetermined position and orientation so that at least a portion of the ion beam may prepare the sample.

With continuing reference to FIG. 1, the ion beam preferably comprises noble gas ions. Non-noble gas ions may be used in other preferred embodiments. Noble gas elements used for the ion beam may include but are not limited to: Argon, Xenon, and Krypton. The ion beam may also comprise a mixture of ions and neutrals. The position and direction of ion beam irradiating means 20 may be changed so that the angle of incidence of the central ion beam axis to the sample may be changed. In preferred embodiments the angle of incidence may have a range of around plus or minus 10 degrees of horizontal. Higher angles of incidence remove material from the sample more quickly while lower angles of incidence produce a smoother surface with fewer artifacts. Ion beam intensity control means 24 is operative to control ion beam irradiating means 20 such that one or more of the following properties of the ion beam may be controlled: energy of the ions produced, number of ions produced per unit time, divergence of the emitted ion beam, and spatial distribution and shape of the emitted ion beam.

Rotation stage 40 is disposed in vacuum chamber 10 in a predetermined position and orientation with respect to central ion beam axis 22. During preparation of the sample, rotation drive 42 may control the rotation of rotation stage 40 around rotation axis 44. Also, during preparation of the sample, ion beam intensity control means 24 may vary the intensity of the ion beam so that at least two different beam intensities may be used during sample preparation. In addition, during preparation of the sample, ion beam tilt control means 26 may vary the tilt angle of the ion beam so that at least two different tilt angles may be used during sample preparation. After the sample has been prepared in the ion beam, chamber cover 18 may be removed; then the sample holder may be removed and the prepared sample may be observed in a microscope.

Rotation drive 42 may be configured to rotate rotation stage 40 through a full 360° of rotation or to rock rotation stage 40 back and forth between two distinct angular positions. In addition, rotation drive 42 may be configured for either continuous or intermittent rotation. Rotation drive 42 may be further configured to measure the rotational position of rotation stage 40 and that measurement or sequence of measurements to control position, speed, or acceleration of rotation stage 40.

Figure 2:
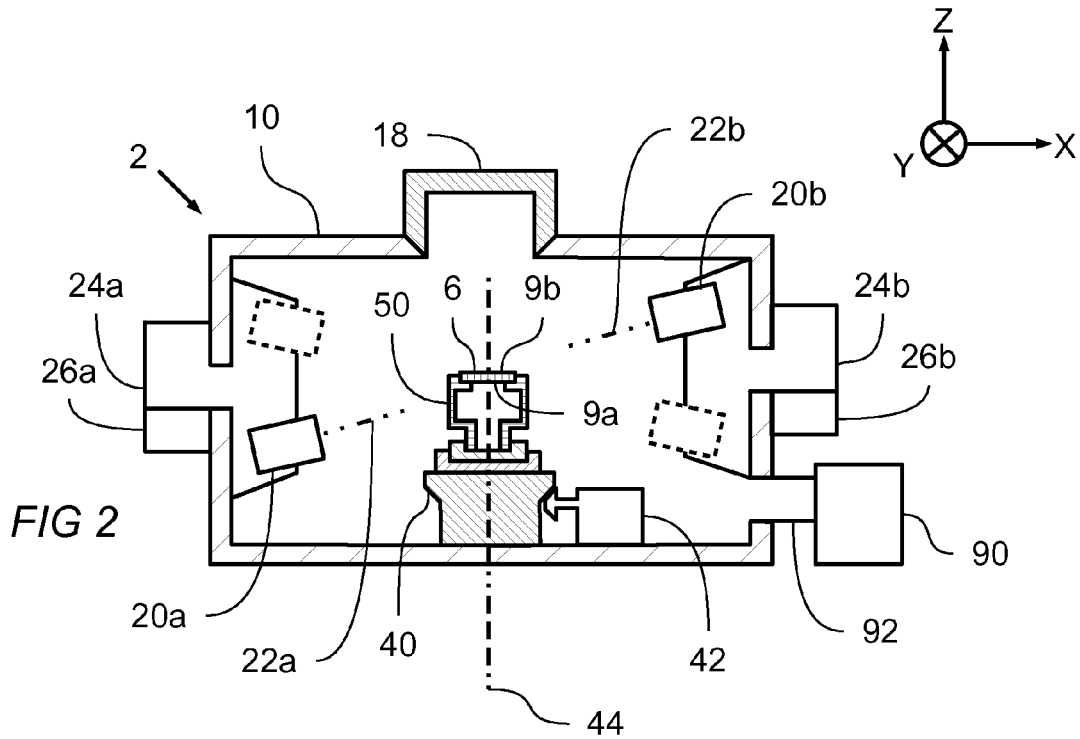
FIG. 2 shows schematic cross sectional view of an ion beam sample preparation apparatus according to another embodiment of the present disclosure.

FIG. 2 shows an embodiment similar to that shown in FIG. 1, having a first ion beam irradiating means 20a and a second ion beam irradiating means 20b, with first ion beam irradiating means having a first central ion beam axis 22a and second ion beam irradiating means having a second central ion beam axis 22b. The embodiment of FIG. 2 further comprises: a first ion beam intensity control means 24a, which is operative to provide at least two different intensities from first ion beam irradiating means 20a; a first ion beam tilt control means 26a, which is operative to provide at least two different tilt angles of ion beam irradiating means 20a; and a second ion beam intensity control means 24b, which is operative to provide at least two different intensities from second ion beam irradiating means 20b; a second ion beam tilt control means 26b, which is operative to provide at least two different tilt angles of ion beam irradiating means 20b.

The apparatus of FIG. 2 shows sample 6 being prepared by both first ion beam irradiating means 20a and second ion beam irradiating means 20b. Sample 6 is shown in FIG. 2 as having a first sample surface 9a and a second sample surface 9b. The embodiment of FIG. 2 shows first ion beam irradiating means 20a preparing first sample surface 9a while second ion beam irradiating means 20b is preparing second sample surface 9b. The preferred embodiment shown in FIG. 2 makes it clear that having multiple ion beam irradiating means enables the apparatus to prepare more than one side of sample 6 at a time and thereby offers speed and efficiency improvements over a single ion beam irradiating means. In other preferred embodiments more than one ion beam may prepare the same side of the sample.

Figure 3:
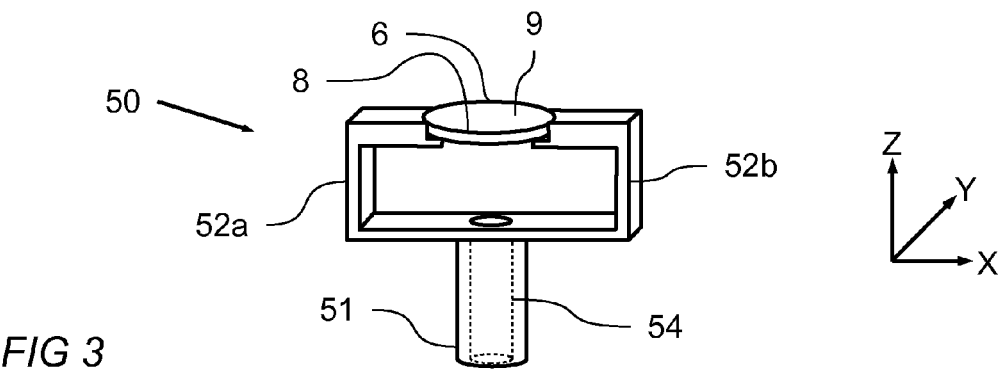
FIG. 3 shows a perspective view of a sample holder holding a sample.

Turning now to FIG. 3, shown is a perspective view of sample holder 50. Sample holder 50 is shown comprising sample holder retained portion 51, a portion of which may be releasably retained by the sample holder retention means of adjustable positioning stage 45 when the sample holder is disposed in the vacuum chamber for sample preparation, and first sample support arm 52a and second sample support arm 52b, which together support and position sample 6. Sample 6 of FIG. 3 is shown having a sample surface 9 and a sample peripheral edge 8. When sample 6 is being prepared in the ion beam a portion of the beam will be directed at sample surface 9, thereby achieving, through the action of the ion beam, both polishing and thinning of sample 6. Sample peripheral edge 8 typically has a smaller dimension than sample surface 9. Prior to preparation, sample 6 will typically have a thin, disk-like, appearance. Also visible in FIG. 3 is sample holder bore 54, which has a generally hollow aspect allowing an unobstructed line of sight from the bottom surface of sample 6 down through the entirety of sample holder retained portion 51. When sample holder 50 is in a retained position, the rotation axis of the rotation stage passes through sample holder bore 54 without intersecting any part of sample holder 50.

Figure 4:
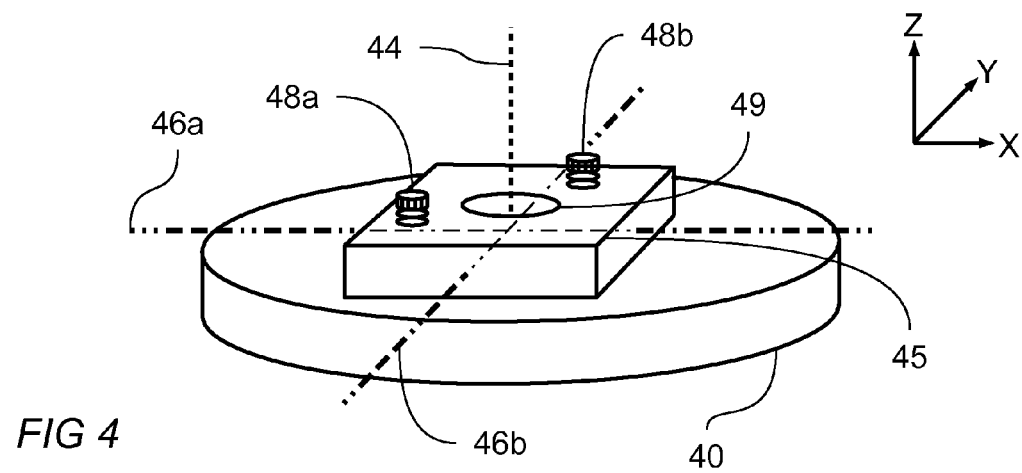
FIG. 4 shows a perspective view of a rotation stage coupled to an adjustable positioning stage prior to retaining a sample holder.

Now with reference to FIG. 4, shown is a close-up perspective view of the portion of rotating stage 40 that is coupled to adjustable positioning stage 45. During the operation of ion beam sample preparation apparatus 2, rotation stage 40 is in a predetermined location within vacuum chamber 10. Adjustable positioning stage 45 is movably coupled to rotation stage 40, thereby enabling adjustment of the position of sample holder retention means 49. The adjustable positioning stage 45 of FIG. 4 comprises: a first position adjustment means 48a which is configured to move the adjustable positioning stage along a first adjustment axis 46a, and a second position adjustment means 48b which is configured to move the adjustable positioning stage along a second adjustment axis 46b, and a sample holder retention means 49, which releasably retains sample holder 50 in the apparatus while the sample is being prepared in one or more ion beams.

Adjustment of first position adjustment means 48a causes adjustable positioning stage 45 to move with respect to rotation stage 40 along first adjustment axis 46a. In a similar fashion, adjustment of second position adjustment means 48b causes adjustable positioning stage 45 to move with respect to rotation stage 40 along second adjustment axis 46b. First and second position adjustment means thereby accomplish micro-positioning of sample holder retention means 49 along first and second adjustment axes. When a sample holder is retained in adjustable positioning stage 45, the position of the sample holder and the position of any sample that may be held by the sample holder may be adjusted using first and second position adjustment means 48a and 48b.

In preferred embodiments, position adjustment means may allow a range of movement along the adjustment axis of about 0.5 millimeters, and incremental adjustments along an adjustment axis can be made, repeatably, as small as 25 micrometers. In other preferred embodiments position adjustment means may allow a range of movement along the adjustment axis of a few millimeters. In other preferred embodiments, incremental adjustments along an adjustment axis can be made with the position adjustment means, repeatably, as small as 10 micrometers. A number of constructions of the adjustable positioning means are possible in which the adjustments may be made by the hand of the operator, including, but not limited to: rack and pinion action; fine-pitch lead-screw action; and, cam and cam-follower action. In addition, electromechanical position adjustment means are also within the spirit and scope of this disclosure including, but not limited to: piezoelectric stepper motor action; stepper motor action; and, servo motor action.

First and second position adjustment means 48a, and 48b, respectively, may be adjusted both prior to installing sample holder and after the sample holder has been installed. When sample holder 50 has been installed into adjustable positioning stage 45, the position of the sample holder may be adjusted using first and second position adjustment means 48a and 48b.

In preferred embodiments, first adjustment axis 46a is positioned to be substantially perpendicular to rotation axis 44, and second adjustment axis 46b is positioned to be substantially perpendicular to rotation axis 44. In preferred embodiments, first adjustment axis 46a and second adjustment axis 46b are positioned substantially perpendicular to each other. The cumulative result of first and second position adjusting means is to allow sample 6 to move within the vacuum chamber relative to the position and direction of one or more ion beams so that different areas of sample 6 may be prepared by the one or more ion beams.

Figure 5:
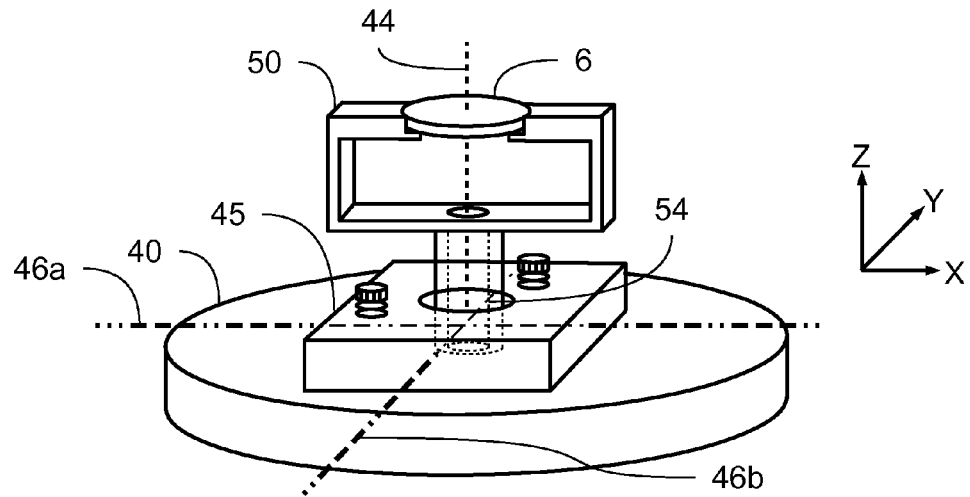
FIG. 5 shows a perspective view of a rotation stage coupled to an adjustable positioning stage with the sample holder in a retained position.

FIG. 5 shows a perspective view in which sample holder retained portion is engaged in sample holder retention means. In preferred embodiments, sample holder retention means 49 may releasably retain sample holder 50 using a friction fit or a spring loaded mechanism. Alternate constructions of sample holder retention means 49 include, but are not limited to threaded and clamping mechanisms. When sample holder 50 is retained in adjustable positioning stage 45, any adjustment made to first position adjustment means 48a will move sample 6 along the direction of first adjustment axis 46a. Also, any adjustment made to second position adjustment means 48b will move sample 6 along the direction of second adjustment axis 46b. FIG. 5 further shows that first and second position adjustment means may be accessed and adjusted while sample holder 50 is in the retained position on adjustable positioning stage 45.

Figure 6:
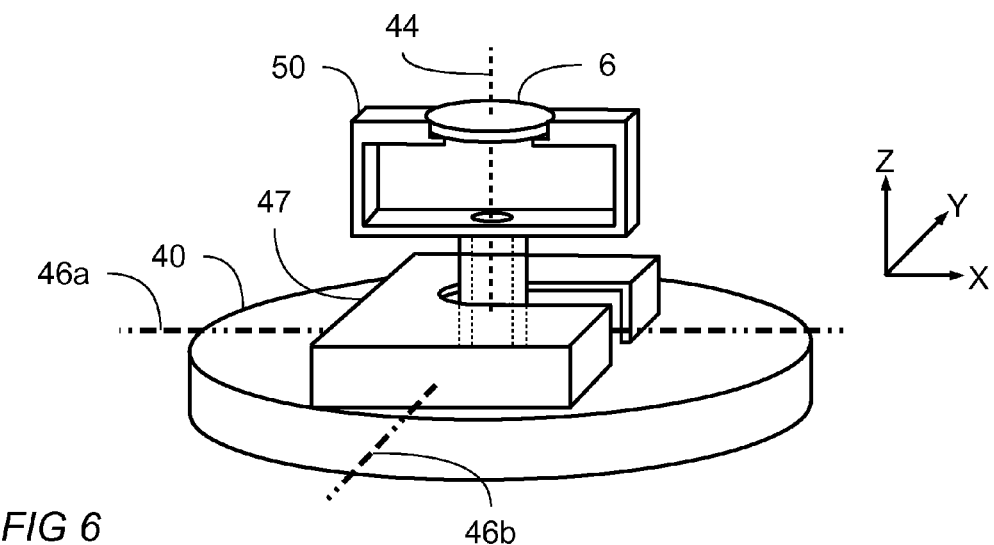
FIG. 6 shows a perspective view of the apparatus of FIG. 5 in which a positioning stage cover has been placed on the rotation stage.

FIG. 6 shows a perspective view of the apparatus of FIG. 5 in which a positioning stage cover 47 has been placed on rotation stage 40 in such a way as to cover the adjustable positioning stage and thereby protect the adjustable positioning stage from sputtered debris as the sample is being prepared by one or more ion beams. Positioning stage cover 47 is further characterized in that it may be installed and removed while sample holder 50 is retained, and it may be removed and reinstalled without moving or otherwise disturbing or touching sample 6.

Figure 7A:
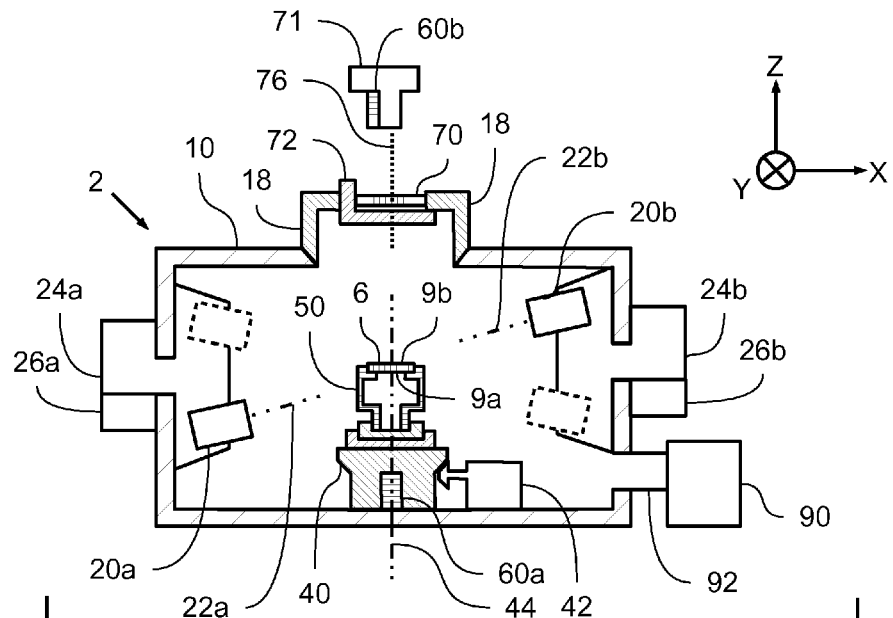
FIG. 7A shows a schematic cross sectional view of an ion beam sample preparation apparatus according to another embodiment of the present disclosure having features that enable viewing of the sample while it is being prepared by the ion beam, with shutter means shown in a shutter closed position.

Turning now to FIG. 7A, shown is a schematic cross sectional view of an ion beam sample preparation apparatus according to another embodiment of the present disclosure, having features that enable viewing of the sample while it is being prepared by the ion beam. The apparatus of FIG. 7A additionally discloses: a vacuum chamber cover 18 comprising: a vacuum tight, optically transparent vacuum window 70, a shutter means 72 disposed between vacuum window 10 and sample holder 50, shutter means 72 further characterized as having both a shutter closed position, in which vacuum window 70 is substantially sealed from the interior of vacuum chamber 10, and a shutter open position, in which direct, line-of-sight viewing of sample 6 is permitted from outside vacuum chamber 10, through vacuum window 70, and onto sample 6 as it is being prepared by one or more ion beams; a sample viewing means 71 having an optical axis 76 directed toward the region of sample 6 being prepared by one or more ion beams, sample viewing means 71 further characterized as providing a magnified and substantially focused view of the region of the sample being prepared by one or more ion beams; a first illumination source 60a, which directs light toward first sample surface 9a, and in which at least a portion of the light strikes the region of sample 6 being prepared by one or more ion beams; and a second illumination source 60b, which directs light toward second sample surface 9b, and in which at least a portion of the light strikes the region of sample 6 being prepared by one or more ion beams.

In the apparatus of FIG. 7A, the rotation stage 40 and adjustable positioning stage are configured to allow at least a portion of light from first illumination source 60a to pass through the sample holder bore and strike first sample surface 9a in the region where the sample is being prepared by one or more ion beams. In preferred embodiments, first and second illumination sources 60a and 60b, respectively, comprise light emitting diodes (LEDs) emitting substantially monochromatic light, light with a broad color spectrum, or any combination both mono-chromatic and broad spectrum. In preferred embodiments, sample viewing means 71 is an optical microscope with appropriate focal length and magnification to view the region of the sample being prepared.

Figure 7B:
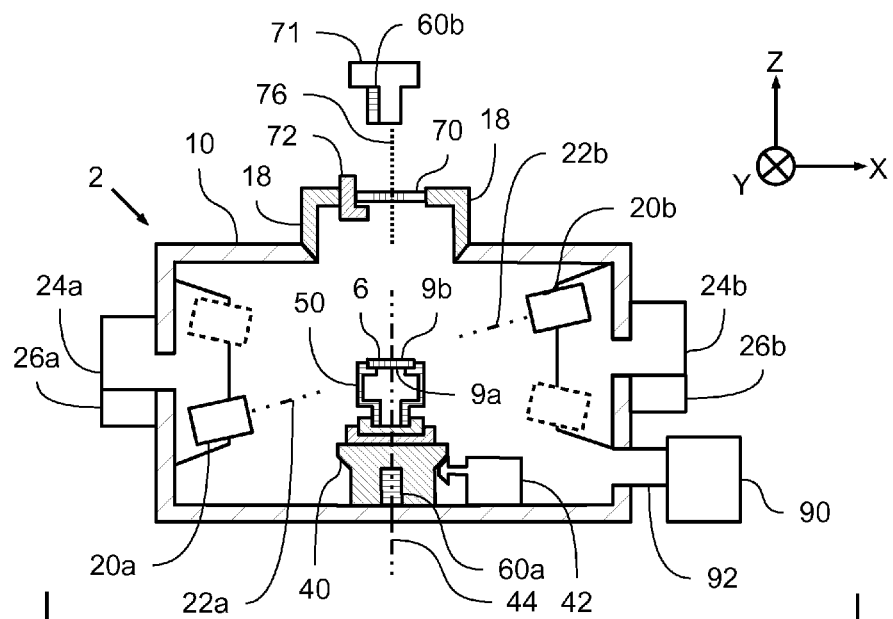
FIG. 7B shows a schematic cross sectional view of the apparatus of FIG. 7A with shutter means shown in a shutter open position.

It can be appreciated, with reference to FIG. 7A, that when shutter means 72 is in the shutter closed position, vacuum window 70 is protected from being fouled or clouded by sputtered material that may be produced in the apparatus as a sample is being prepared by the one or more ion beams. Shutter means 72 may be manipulated into the shutter open position, as shown in FIG. 7B, when the operator desires to view the progress of the sample using sample viewing means 71. After sample viewing, shutter means 72 may be returned to the shutter closed position of FIG. 7A, thereby minimizing the amount of sputtered material allowed to build up on vacuum window 70.

Use of the apparatus shown in FIG. 1 through FIG. 7B may proceed with reference to the following steps: outside of the vacuum chamber a sample may be mounted to a sample holder; with the chamber cover removed, the sample and sample holder combination may be set in the sample holder retention means of the adjustable positioning stage, and the first and second position adjustment means may be adjusted by the operator to move the sample to a position; if desired, the positioning stage cover may then be placed over the adjustable positioning stage; the chamber cover may then be replaced; the vacuum pump means may then be operated to evacuate the vacuum chamber through the pumping manifold, thereby obtaining vacuum levels appropriate for ion beam milling; the ion beam irradiating means may then be operated to prepare the sample. Periodically, the operator of the apparatus may check on the progress and location of the prepared portion of the sample. If the apparatus is equipped with vacuum window, shutter, illumination, and sample viewing means, then the shutter may be opened and the sample viewed directly by the operator without needing to remove the chamber cover. If the apparatus is not equipped with vacuum window etc., then the chamber can be opened to inspect the progress of the sample preparation. If the operator judges that the desired region of the sample is not being prepared, then the operator may determine that the first or second position adjustment means need to be adjusted to expose and prepare the desired sample region. If necessary, ion beam irradiating means may be turned off, the vacuum chamber may be returned to ambient atmospheric pressure, the chamber cover removed, the positioning stage cover removed if necessary, and then the first and second position adjusting means may be adjusted by the operator to adjust the position of the sample. The sample may then be returned to the vacuum chamber and the process repeated as needed until the sample is prepared as desired. A microscope may be then fitted with the sample holder for observation of the sample's region of interest.

Figure 8A:
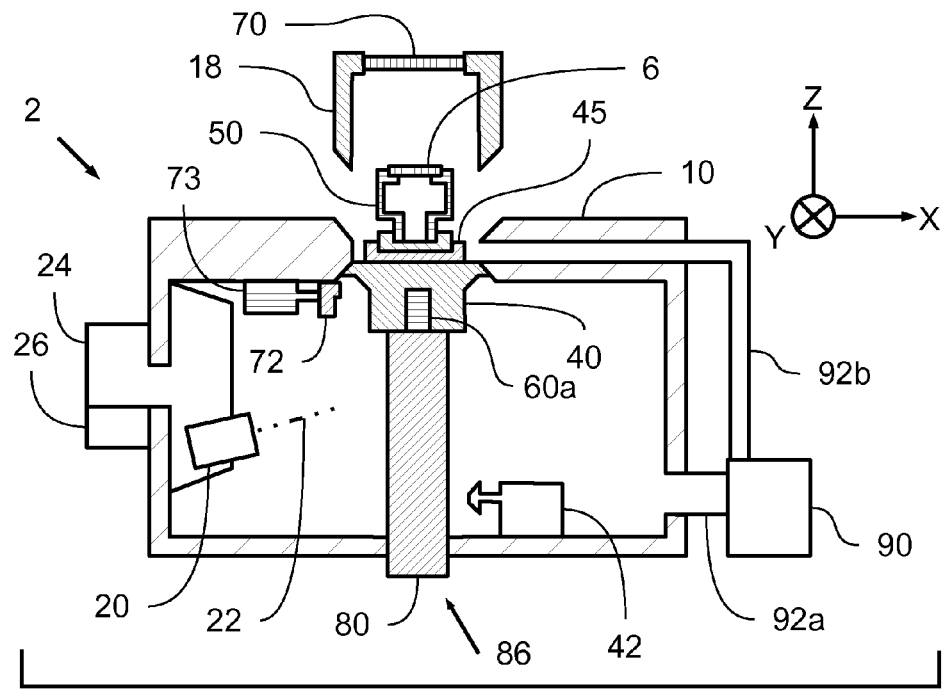
FIG. 8A shows a schematic cross sectional view of an ion beam sample preparation apparatus according to another embodiment of the present disclosure featuring a rotation stage lifting means. The apparatus of FIG. 8A is shown with a rotation stage lifting means in a raised position and the shutter means in a shutter open position.

Shown now in FIG. 8A is a schematic cross sectional view of an ion beam sample preparation apparatus 2 according to another embodiment of the present disclosure, featuring a rotation stage lifting means 80. In the apparatus of FIG. 8A, a rotation stage lifting means is shown in a raised position 86. While in raised position 86, sample holder 50 may be installed or removed from adjustable positioning stage 45. Also, while in raised position 86, first position adjustment means and second position adjustment means of the adjustable positioning stage 45 may be adjusted, thereby facilitating the preparation of a region of interest in sample 6. The apparatus of FIG. 8A is shown comprising: a vacuum chamber 10, in which a sample may be prepared; a removable and replaceable chamber cover 18, having an optically transparent vacuum window 70; an ion beam irradiating means 20, which creates and directs an ion beam having a central ion beam axis 22 toward sample 6; an ion beam intensity control means 24, which is operative to provide at least two different ion beam intensities; an ion beam tilt control means 26, which is operative to provide at least two different tilt angles of ion beam irradiating means 20; a first pumping manifold 92a and a pumping means 90, which together bring vacuum chamber 10 to vacuum levels appropriate for ion beam milling; a rotation stage 40 coupled to an adjustable positioning stage 45, in which sample holder 50 may be held; a rotation stage lifting means 80 which is operably coupled to rotation stage 40, rotation stage lifting means 80 being further characterized in having a raised position 86, in which vacuum sealing features engage between vacuum chamber 10 and rotation stage 40 to maintain vacuum conditions inside vacuum chamber 10; a shutter means 72 having a shutter open position and a shutter closed position, the shutter open position further characterized as permitting a direct, line-of-sight viewing of sample 6 from outside vacuum chamber 10, through vacuum window 70, and onto sample 6 as it is being prepared by the ion beam; a shutter actuation 73 means operably coupled to shutter means 72 to provide both a shutter open position and a shutter closed position; and, a first illumination source 60a, which directs light toward sample 6, at least a portion of which strikes the sample.

Figure 8B:
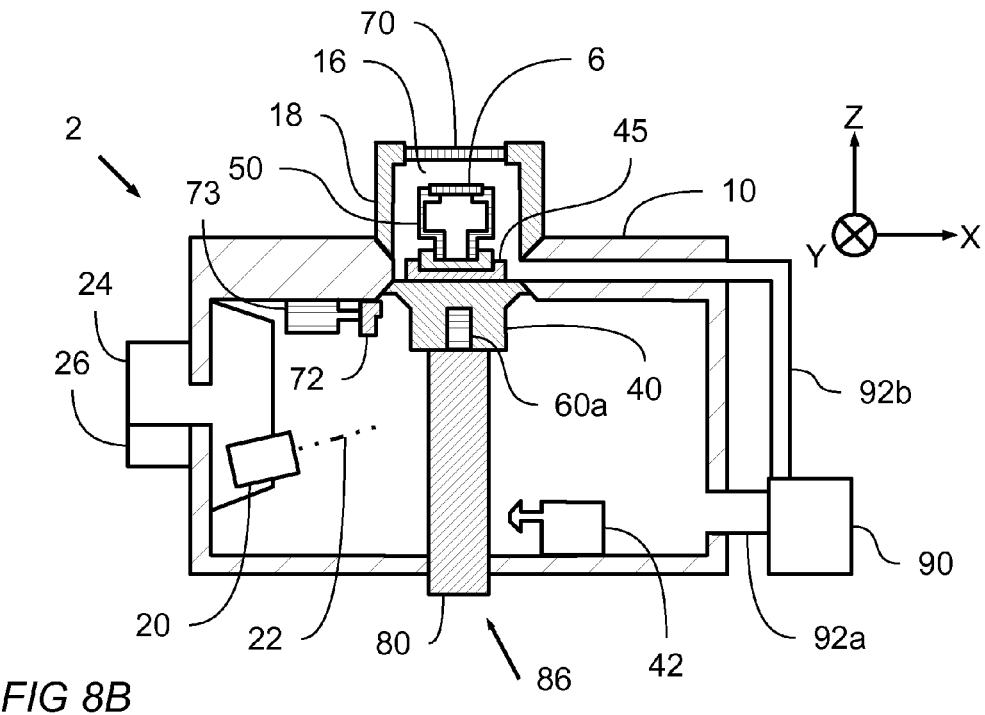
FIG. 8B shows the apparatus of FIG. 8A with the chamber cover in place and creating a loading chamber.

FIG. 8B shows the apparatus of FIG. 8A with chamber cover 18 installed on vacuum chamber 10 and thereby creating loading chamber 16, which is isolated from both the outside atmosphere and the remainder of vacuum chamber 10. In a preferred embodiment, when chamber cover 18 is in place to seal the loading chamber from the outside atmosphere, the volume of loading chamber 16 is substantially smaller than the volume of vacuum chamber 10. When the apparatus is configured as in FIG. 8B, second pumping manifold 92b and pumping means 90 may be used to evacuate loading chamber 16 in preparation for lowering sample 6 into the processing position.

Figure 8C:
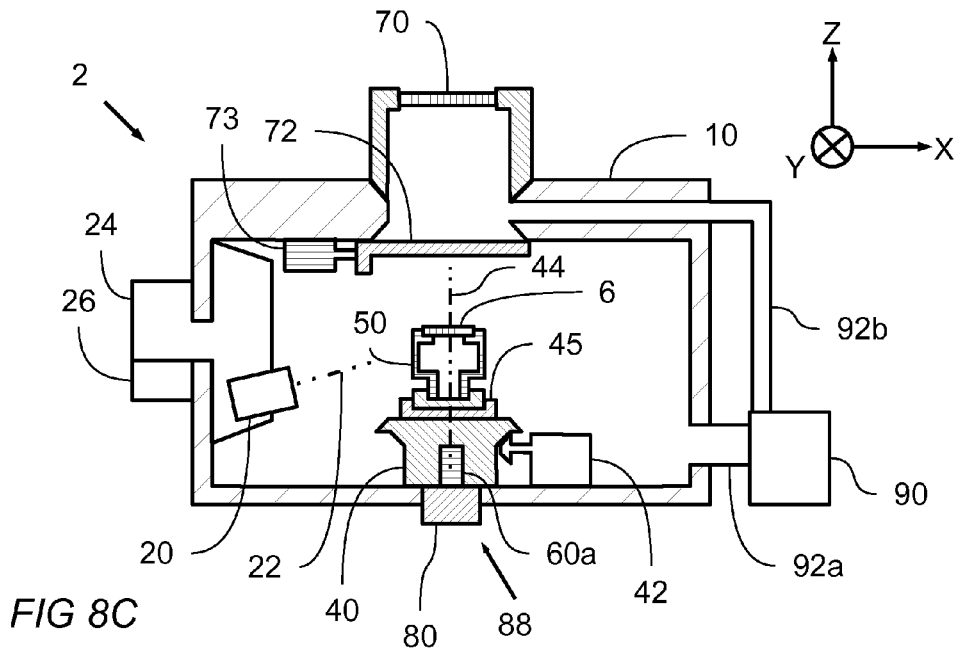
FIG. 8C shows the apparatus of FIG. 8A with the rotation stage lifting means in a processing position and the shutter means in a shutter closed position.

FIG. 8C shows the same apparatus as FIG. 8A and FIG. 8B, however, rotation stage lifting means 80 has operated to move the rotation stage into a processing position 88. When in processing position 88, rotation drive 42 is engaged with rotation stage 40 and is operable to rotate around rotation axis 44. Processing position 88 disposes sample 6 in a position where one or more surfaces of sample 6 may be processed by the ion beam. FIG. 8C further shows shutter means 72 in a shutter closed position, in which vacuum window 70 may be isolated from the rest of vacuum chamber 10 thereby minimizing the amount of sputtered material allowed to build up on vacuum window 70.

Figure 8D:
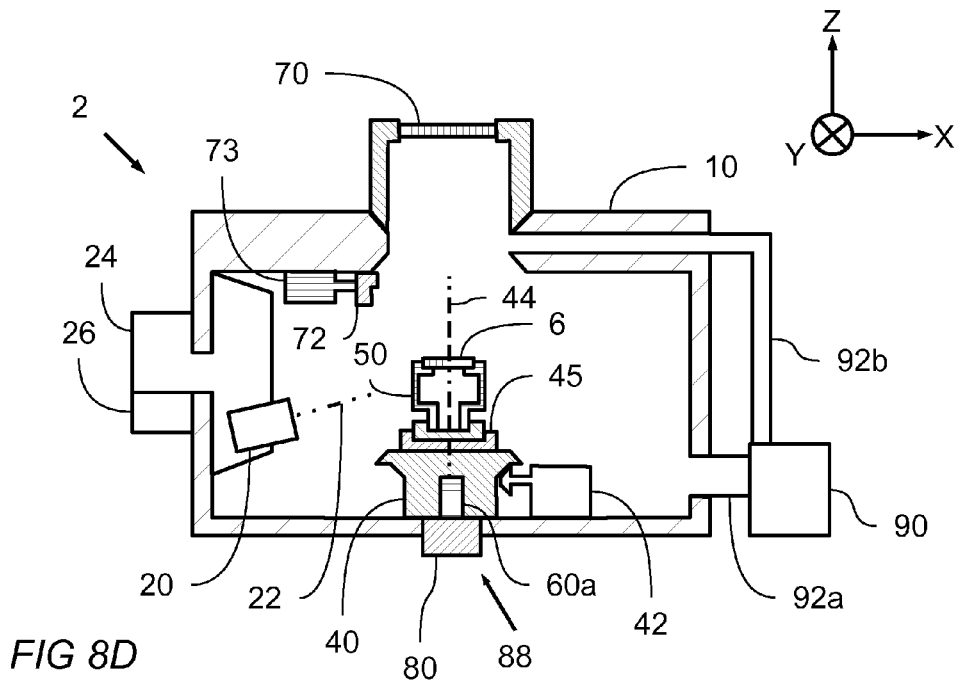
FIG. 8D shows the apparatus of FIG. 8A with the rotation stage lifting means in a processing position and the shutter means in a shutter open position and ready for observation of the sample from outside the vacuum chamber through the vacuum window.

FIG. 8D shows the same apparatus as FIG. 8A, FIG. 8B, and FIG. 8C, however, shutter actuation means 73 has operated to move shutter means 72 into a shutter open position that allows direct, line-of-sight viewing, through vacuum window 70 and onto the sample being prepared in the ion beam. When necessary, the sample may be viewed while undergoing processing through vacuum window 70 with the shutter means 72 in a shutter open position. A variety of means may be used to view the sample including, but not limited to: optical microscope, still camera, digital image capture, video, and other means of capturing images for either immediate or time-delayed analysis.

In can be appreciated that the apparatus of FIGS. 8A, 8B, 8C, and 8D allows certain desirable efficiencies. Instead of venting the entire vacuum chamber when a positioning adjustment of the sample needs to be made, rotation stage lifting means 80 may be operated to raise the sample into the loading chamber 16. In preferred embodiments, the volume of the loading chamber is much smaller that the volume of the vacuum chamber. Vacuum conditions are maintained in the remainder of the vacuum chamber when the rotation stage is in the raised position. Venting and evacuating the small volume of the loading chamber takes much less time than it does to vent and evacuate the entire chamber. When the loading chamber has been evacuated to pressures appropriate for ion beam milling, the rotation stage lifting means may be operated to move the sample into the processing position, and the sample may again be prepared in the ion beam.

Figure 9:
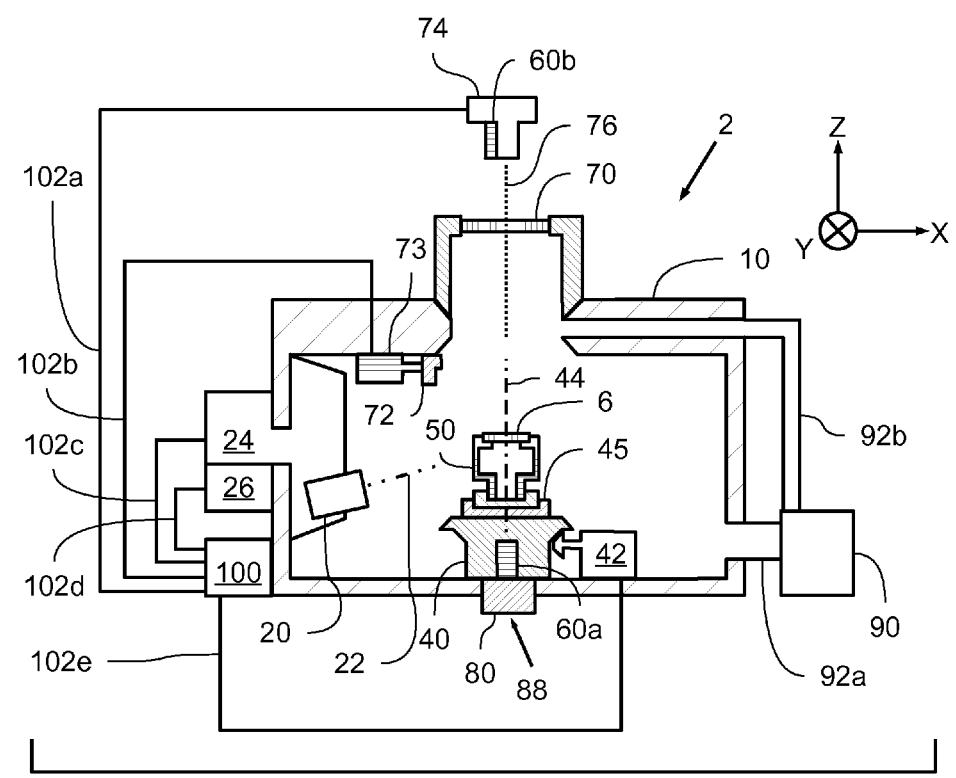
FIG. 9 shows a schematic cross sectional view of an ion beam sample preparation apparatus according to another embodiment of the present disclosure featuring an instrument controller which is communicating with and controlling the systems of the apparatus.

Turning now to FIG. 9, shown is an embodiment of the apparatus of FIG. 8A through FIG. 8D which additionally comprises: a sample imaging means 74 having an optical axis 76 directed toward the region described by the intersection of rotation axis 44 with sample 6; a second illumination source 60b, which directs light toward sample 6, at least a portion of which strikes the sample; an instrument controller 100 which: communicates with and coordinates the actions of sample imaging means 74 through first communications channel 102a; communicates with and coordinates the actions of shutter actuation means 73 through second communications channel 102b; communicates with and coordinates the actions of ion beam intensity control means 24 through third communications channel 102c; communicates with and coordinates the actions of ion beam tilt control means 26 through fourth communications channel 102d; communicates with and coordinates the actions of rotation drive 42 through fifth communications channel 102e.

The ion beam sample preparation apparatus 2 shown in FIG. 9 enables numerous improvements in both the quality of prepared samples and in the efficiency of their preparation. Sample imaging means 74 may take different forms with different features, as may be appropriate for the imaging task. In preferred embodiments, sample imaging means 74 is operable to acquire images and communicate image data to instrument controller 100. Sample imaging means 74 may also process acquired images, extract features from the acquired images, and communicate those extracted features to instrument controller 100. Instrument controller 100 may then use image data, processed image data, and features extracted from image data in controlling those subsystems with which instrument controller 100 may be in communication. Instrument controller 100 may also store image data, processed image data, and extracted image features for later use.

In preferred embodiments, sample imaging means 74 comprises: a digital image sensor, a lens system coupled to said digital image sensor and focused on at least a portion of the sample being prepared in the ion beam; and a zoom capability which may be either optical in nature so as to operate on the lensing system, or digital in nature so as to operate on the digital image that is acquired. In preferred embodiments, first communications channel 102a carries data bidirectionally between instrument controller 100 and sample imaging means 74. Instrument controller 100 may thereby both trigger the acquisition of images through sample imaging means 74 and receive data derived from the act of acquiring an image. In certain preferred embodiments, sample imaging means 74 may control first illumination source 60a and second illumination source 60b, and thereby have greater control over the quality of the sample image acquired. Sample imaging means 74 may additionally comprise an operator display which may show an operator of the apparatus an image or sequence of images from the sample as it is being prepared in the ion beam. Sample imaging means 74 may additionally display stored images acquired previously.

In other preferred embodiments, images acquired by sample imaging means 74 may be processed to extract features of interest relating to the process of preparing a sample in the ion beam. In one preferred embodiment, first illumination source 60a may provide illumination of sample 6 as sample imaging means 74 acquires an image. As the sample is being processed by the ion beam, it will gradually become thinner. Eventually a perforation of the sample will start to form. When the sample is backlit, such a perforation will show up as a bright spot, whereas non-perforated regions of the sample will show up much darker on an image. In another preferred embodiment, first and second illumination sources 60a and 60b, respectively, may illuminate the sample. As the sample thins, but prior to the perforation of the sample, interference rings located around the thinnest area of the sample may become visible on an image. In addition, color changes of the interference rings may be observed prior to the perforation of the sample by the ion beam. These images features, and others, may be extracted from a captured image or sequence of images and may be used by instrument controller 100 in the operation of the apparatus.

Through second communications channel 102b, instrument controller 100 is operative to control shutter actuation means 73, and thereby provide at least two positions of shutter means 72. In addition, second communications channel 102b may be operative to send data to instrument controller 100 that may indicate what position shutter means 72 may be in. Instrument controller 100 may thereby both control and observe the operation of shutter actuation means 73 and shutter means 72.

Through third communications channel 102c, instrument controller 100 is operative to control ion beam intensity control means 24, thereby providing at least two different intensities of ion beam. Third communications channel 102c may carry bidirectional data between instrument controller 100 and ion beam intensity control means 24, and may thereby both control and observe the operation of ion beam intensity control means 24.

Through fourth communications channel 102d, instrument controller 100 is operative to control ion beam tilt control means 26, thereby providing at least two different tilt angles of the ion beam. Fourth communications channel 102d may carry bidirectional data between instrument controller 100 and ion beam tilt control means 26, and may thereby both control and observe the operation of ion beam tilt control means 26.

Through fifth communications channel 102e, instrument controller 100 is operative to control rotation drive 42. Instrument controller 100 may thereby control the position, speed, and acceleration of rotation stage 40. Fifth communications channel 102e may carry bidirectional data between instrument controller 100 and rotation drive 42 so that instrument controller 100 may both control and observe the operation of rotation stage 40.

Figure 10:
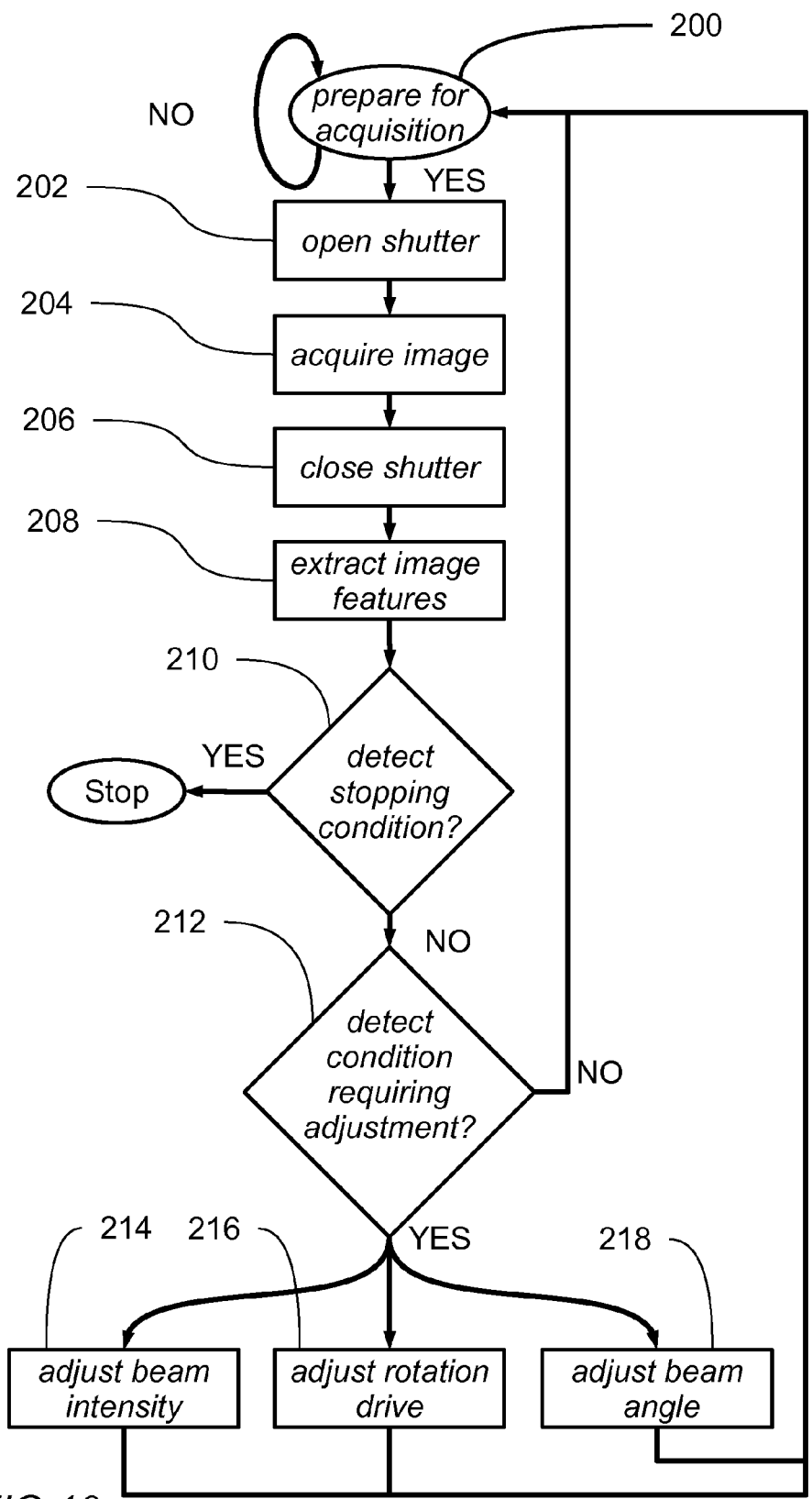
FIG. 10 shows an operational flow chart of a periodically executed observation and control process operating in the apparatus of FIG. 9.

FIG. 10 shows a flowchart of the operation of the apparatus of FIG. 9 according to a preferred embodiment of the disclosure. The process steps of FIG. 10 can be understood with reference to instrument controller 100 acting as both observer and controller of the subsystems of the apparatus. Starting with process step of prepare for acquisition 200, instrument controller 100 starts to prepare the apparatus to capture an image of the sample being prepared. In preferred embodiments, acquisition trigger? 200 may happen at predetermined times or at predetermined rotation angles. The process then moves to process step open shutter 202, during which time shutter means 72 may be caused to move to the shutter open position. Moving on to process step acquire image 204, sample imaging means 74 may be caused to acquire an image, after which process step close shutter 206 may move shutter means 72 to the shutter closed position. Process step extract image features 208 may then extract features of interest from the newly acquired image. If one or more of the extracted features indicate that the sample is finished, then process step detect stopping condition? 210 identifies the stopping condition and stops the process. If no stopping condition was detected, then the process moves on to process step detect condition requiring adjustment? 212 to decide if any adjustments must be made to the apparatus. If no adjustments are necessary, then the process transitions back to process step acquisition trigger? 200 and repeats. If adjustment is necessary, then one or any combination of the following three process steps may be triggered: adjust beam intensity 214; adjust rotation drive 216; and, adjust beam angle 218. After adjustments are made, the process transitions back to process step acquisition trigger? 200 and repeats. During process step adjust beam intensity 214, ion beam intensity control means 24 may be caused to increase or decrease the intensity of the ion beam. During process step adjust rotation drive 216, rotation drive 42 may be caused to increase or decrease the rotational position, the rotation speed, or the acceleration of rotation stage 40. During process step adjust beam angle 218, ion beam tilt control means 26 may be caused to adjust the angle with which central ion beam axis 22 strikes sample 6.

Figure 11:
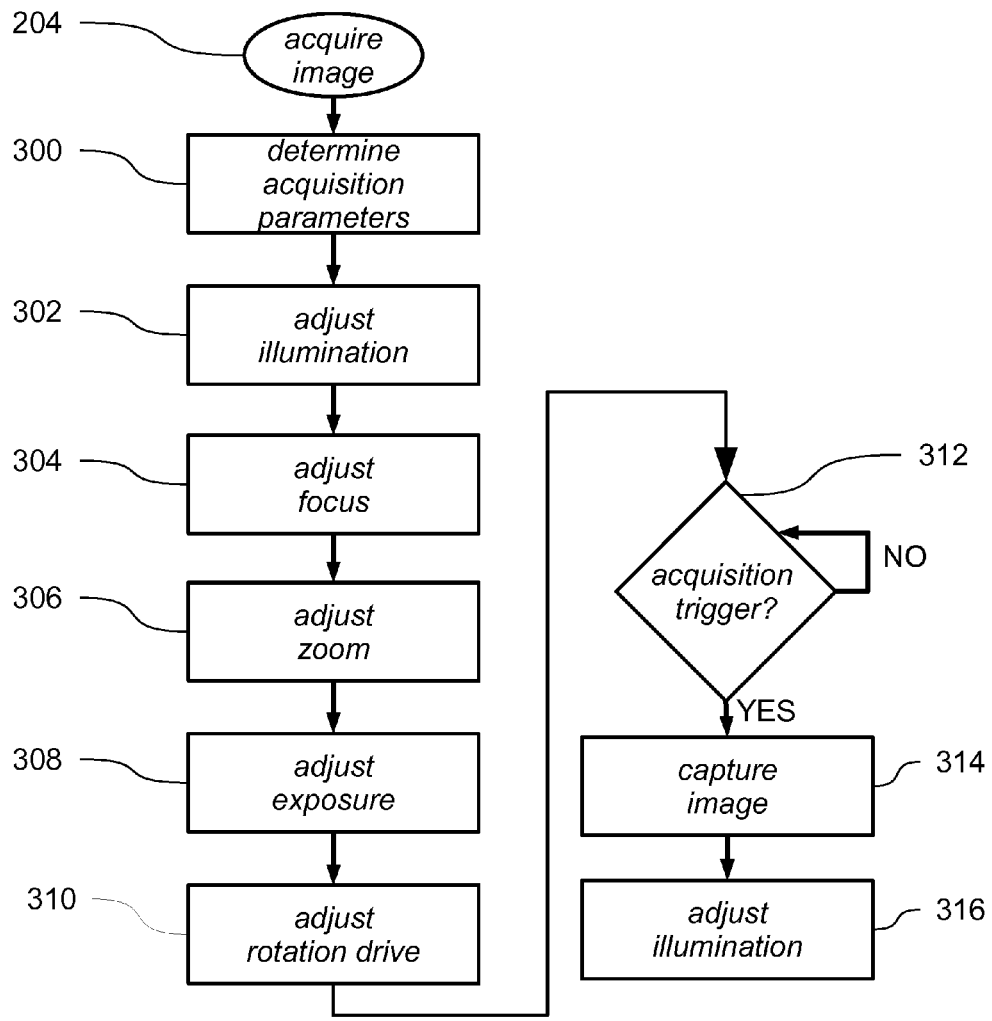
FIG. 11 shows an operational flow chart of the image acquisition process operating in the apparatus of FIG. 9.

Process step acquire image 204 can now be better understood with reference to the flowchart of FIG. 11. The flowchart of FIG. 11 shows that a number of sub-steps may be beneficially performed to complete the process step of acquire image 204. In process step determine acquisition parameters 300, sample imaging means 74 retrieves or derives parameters which control the acquisition of the image. Then process step adjust illumination 302 uses retrieved or determined parameters to adjust the illumination provided by first illumination source 60a, or second illumination source 60b, or both illumination sources. Process step adjust focus 304 then uses retrieved or determined parameters to adjust the focus properties of sample imaging means 74. Process step adjust zoom 306 uses retrieved or determined parameters to adjust the zoom properties of sample imaging means 74. Process step adjust exposure 308 uses retrieved or determined parameters to adjust exposure properties of sample imaging means 74. Process step adjust rotation drive 310 may adjust the position, speed, and acceleration of the rotation stage, according to retrieved or determined parameters. In preferred embodiments the apparatus may slow down or stop the rotation stage prior to image capture. Next, the apparatus waits at process step acquisition trigger? for a precisely predetermined time or a precisely determined rotation angle to occur. When acquisition trigger? does occur the process will transition to process step capture image 314, where the image will be captured. The image may be stored to nonvolatile storage or sent via communication channel elsewhere for other uses. After capture is complete the process advances to process step adjust illumination 316 so that the first and second illumination sources may be adjusted, which may include being turned off. Thereafter, the process embodied by the flowchart of FIG. 11 is complete.

The apparatus of FIG. 9 makes many beneficial capabilities and features possible. One preferred benefit is that sequences of images may be captured. When one or more ion beams are directed at the sample, imaging means 74 may capture sequential images of the sample which will correspond to deeper and deeper regions of the sample because the ion beam is removing material from the sample between successive images. A 3D reconstruction of the sample may therefor be made from a sequence of images acquired by the embodiment of FIG. 9.

Additional image processing may be used on acquired images. In a preferred embodiment, images captured at different rotation angles may each be programmatically rotated by instrument controller 100 to appear as though all images were captured at the same angle. Sequences of images processed in this way would not appear to rotate at all as the sample is being processed and images are being acquired. When viewed by an operator, images processed in the way described greatly enhance the usability of the apparatus.

Figure 12:
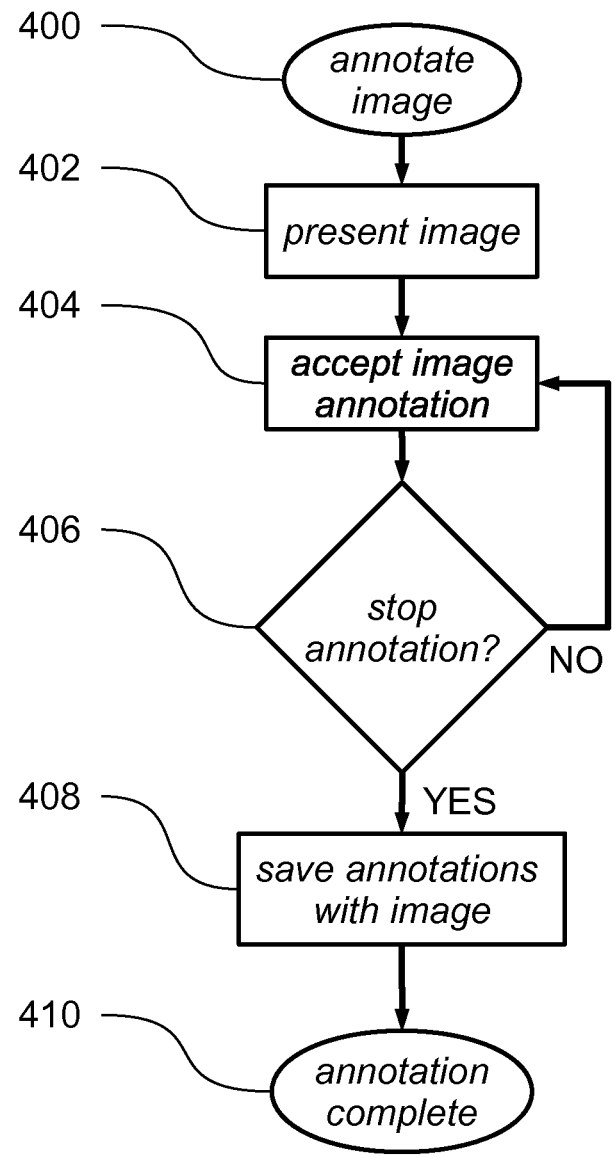
FIG. 12 shows a flowchart of a beneficial aspect of another embodiment according to the present disclosure.

Turning now to FIG. 12, shown is a flowchart of a beneficial aspect of another embodiment according to the present disclosure. The process of FIG. 12 may be carried out by an operator of the ion beam sample preparation apparatus 2 of FIG. 9 in which instrument controller 100 further comprises: a display system for presenting an image to an operator; an input system operable to accept annotations created by an operator; and a storage system operable to save the annotation data with the image. When a sample has been prepared it is often very useful to have a way of recording where the region of interest is or where various features of interest are in the prepared sample. This can be efficiently done by an operator of the ion beam apparatus by following the process of FIG. 12. First process step annotate image 400 is started. Based upon operator selection, or automatically at the end of sample processing, process step present image 402 may present an image that was acquired by sample imaging means 74 to the operator by means of the display system of instrument controller 100. In process step accept image annotation 404, the operator may enter one or more pieces of annotation data using the input system of instrument controller means 100. In preferred embodiments annotation data may specify one or any combination of the following: x and y coordinates of one or more points of interest, unique indicia for each annotation accepted such as incremental numbering or lettering, centroid location of one or more features of interest, the location and extent of a two dimensional sub region of the image containing one or more features of interest, and a classification or other description of the type of feature present in the current annotation. Annotations may be in the form of human readable text, graphics, and images, or may be in a machine readable format adapted to facilitate exchange with other equipment. Process step stop annotation? 406 permits a plurality of annotations to be made for each image. When no more annotations need to be made, process step save annotations with image 408 saves all annotations in the storage system of instrument controller 100 in such a way that the annotations are associated with the image. Process step annotation complete 410 ends this process.

A sample which has been prepared in the ion beam, has been imaged, and also has been annotated according to the process of FIG. 12 may thereafter be transferred to a microscope for observation. The operator of the microscope may derive significant benefits from using the annotated image when locating, magnifying, focusing, and observing the sample in the microscope equipment.

Although the present invention has been described in considerable detail with reference to certain preferred versions thereof, other versions are possible. It may be desirable to combine features shown in various embodiments into a single embodiment. A different number and configuration of features may be used to construct embodiments of ion beam sample preparation apparatus that are entirely within the spirit and scope of the present disclosure. Therefor, the spirit and scope of the appended claims should not be limited to the description of the preferred versions contained herein.

Any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" in the claims herein is not intended to invoke the provisions of 35 U.S.C. Section 112, Paragraph 6.

The invention claimed is:

1. An ion beam sample preparation apparatus comprising:
a) a first ion beam irradiating means disposed in a vacuum chamber and directing a first ion beam toward said sample, said first ion beam irradiating means operatively coupled to a first ion beam intensity control means, said first ion beam having a first central ion beam axis, said first ion beam intensity control means operative to produce at least two different ion beam intensities;
b) a first ion beam tilt control means operatively coupled to said first ion beam irradiating means and configured to provide at least two different tilt angles of said first ion beam irradiating means;
c) a rotation stage disposed inside said vacuum chamber having a rotation axis and coupled to a rotation drive, said rotation drive operative to rotate said rotation stage around said rotation axis, said rotation axis being positioned to intersect a portion of said first ion beam;
d) an adjustable positioning stage that is adjustably coupled to said rotation stage, said adjustable positioning stage comprising a sample holder retention means configured to releasably retain a sample holder, said sample holder comprising: a sample holder retained portion; at least one sample support arm configured to support said sample; and a sample holder bore that allows an unobstructed line of sight through the entirety of sample holder retained portion onto said sample being held by said one or more sample support arms; said sample holder further characterized as positioning said sample so that said rotation axis and said first central ion beam axis both intersect substantially the same portion of said sample that is being prepared in said first ion beam; said sample holder further characterized in that no portion of said sample support arm is intersected by said rotation axis while said sample is being prepared by said ion beam;

e) said adjustable positioning stage further comprising: a first position adjustment means configured to move said adjustable positioning stage along a first adjustment axis; and, a second position adjustment means configured to move said adjustable positioning stage along a second adjustment axis;

f) a vacuum-tight optically-transparent vacuum window disposed to permit direct, line-of-sight viewing from outside the vacuum chamber of at least a portion of said sample while said sample is being prepared in said first ion beam; and, a shutter means disposed between said vacuum window and said sample holder; said shutter means further characterized as having a shutter closed position in which said vacuum window is substantially sealed from the interior of said vacuum chamber, and said shutter means further characterized as having a shutter open position that permits direct, line-of-sight viewing from outside the vacuum chamber of at least a portion of said sample while said sample is being prepared in said first ion beam;

g) a first illumination source directing light through said sample holder bore toward said sample and further characterized in that at least a portion of the light emitted by said first illumination source strikes at least a portion of said sample while said sample is being prepared in said first ion beam;

h) a sample viewing means having an optical axis directed toward the region where said first central ion beam axis substantially intersects said rotation axis, said sample viewing means further characterized as providing a magnified and substantially focused view of the region of said sample being prepared by said first ion beam.

2. The apparatus of claim 1 in which said first illumination source is further characterized as producing substantially monochromatic light.

3. The apparatus of claim 1 further comprising: a second illumination source directing light toward said sample and further characterized in that at least a portion of the light emitted by said second illumination source strikes at least a portion of said sample while said sample is being prepared in said first ion beam.

4. The apparatus of claim 1 further comprising: a sample imaging means that is operative to capture one or more images made available by said sample viewing means.

5. The apparatus of claim 4 in which said sample imaging means is operative to save one or more previously captured images.

6. The apparatus of claim 5 further characterized in that the sample imaging means is operative to save one or more unique indicia with each said one or more previously captured images.

7. The apparatus of claim 6 in which said sample imaging means is operative to display said one or more previously captured images.

8. The apparatus of claim 7 further characterized in that the sample imaging means is operative to receive said one or more unique indicia and display said one or more previously captured images corresponding with said one or more unique indicia.

9. The apparatus of claim 7 further characterized in that the sample imaging means is operative to receive one or more annotations identifying the location of one or more regions of interest within said one or more previously captured images and saving said one or more annotations with said one or more previously captured images.

10. An ion beam sample preparation apparatus comprising:

a) a first ion beam irradiating means disposed in a vacuum chamber and directing a first ion beam toward said sample, said first ion beam irradiating means operatively coupled to a first ion beam intensity control means, said first ion beam having a first central ion beam axis, said first ion beam intensity control means operative to produce at least two different ion beam intensities;

b) a first ion beam tilt control means operatively coupled to said first ion beam irradiating means and configured to provide at least two different tilt angles of said first ion beam irradiating means;

c) a rotation stage disposed inside said vacuum chamber having a rotation axis and coupled to a rotation drive, said rotation drive operative to rotate said rotation stage around said rotation axis, said rotation axis being positioned to intersect a portion of said first ion beam;

d) an adjustable positioning stage that is adjustably coupled to said rotation stage, said adjustable positioning stage comprising a sample holder retention means configured to releasably retain a sample holder, said sample holder comprising: a sample holder retained portion; at least one sample support arm configured to support said sample; and a sample holder bore that allows an unobstructed line of sight through the entirety of sample holder retained portion onto said sample being held by said one or more sample support arms; said sample holder further characterized as positioning said sample so that said rotation axis and said first central ion beam axis both intersect substantially the same portion of said sample that is being prepared in said first ion beam; said sample holder further characterized in that no portion of said sample support arm is intersected by said rotation axis while said sample is being prepared by said ion beam;

e) said adjustable positioning stage further comprising: a first position adjustment means configured to move said adjustable positioning stage along a first adjustment axis; and a second position adjustment means configured to move said adjustable positioning stage along a second adjustment axis;

f) a vacuum-tight optically-transparent vacuum window disposed to permit direct, line-of-sight viewing from outside the vacuum chamber of at least a portion of said sample while said sample is being prepared in said first ion beam; and a shutter means disposed between said vacuum window and said sample holder; said shutter means further characterized as having a shutter closed position in which said vacuum window is substantially sealed from the interior of said vacuum chamber, and said shutter means further characterized as having a shutter open position that permits direct, line-of-sight viewing from outside the vacuum chamber of at least a portion of said sample while said sample is being prepared in said first ion beam;

g) a first illumination source directing light toward said sample and further characterized in that at least a portion of the light emitted by said first illumination source strikes at least a portion of said sample while said sample is being prepared in said first ion beam;

h) a sample viewing means having an optical axis directed toward the region where said first central ion beam axis substantially intersects said rotation axis, said sample viewing means further characterized as providing a magnified and substantially focused view of the region of said sample being prepared by said first ion beam;

i) a sample imaging means that is operative to capture one or more images made available by said sample viewing means, said sample imaging means further characterized as being operatively coupled to a first communications channel and being responsive to said communications channel for capturing one or more images and communicating one or more captured images over said first communications channel;

j) an instrument controller that is operative to: communicate with and control the actions of said sample imaging means through said first communications channel; communicate with and control the actions of a shutter actuation means through a second communications channel, said shutter actuation means being operative to move said shutter means between said shutter open position and said shutter closed position in response to communications received through said second communications channel.

11. The apparatus of claim 10 further characterized in that the instrument controller is operative to communicate with and control the actions of said first ion beam intensity control means through a third communications channel, the first ion beam intensity control means being operative to change the intensity of said first ion beam in response to communications received through said third communications channel.

12. The apparatus of claim 10 further characterized in that the instrument controller is operative to communicate with and control the actions of said first ion beam tilt control means through a fourth communications channel, said first ion beam tilt control means being operative to change the intensity of said first ion beam in response to communications received through said fourth communications channel.

13. The apparatus of claim 10 further characterized in that the instrument controller is operative to communicate with and control the actions of said rotation drive through a fifth communications channel, said rotation drive being operative to change the position of said rotation stage in response to communications received through said fifth communications channel.

14. The apparatus of claim 10 further characterized in that:
a) the instrument controller is operative to communicate with and control the actions of said first ion beam intensity control means through a third communications channel, the first ion beam intensity control means being operative to change the intensity of said first ion beam in response to communications received through said third communications channel;
b) the instrument controller is operative to communicate with and control the actions of said first ion beam tilt control means through a fourth communications channel, said first ion beam tilt control means being operative to change the intensity of said first ion beam in response to communications received through said fourth communications channel; and
c) the instrument controller is operative to communicate with and control the actions of said rotation drive through a fifth communications channel, said rotation drive being operative to change the position of said rotation stage in response to communications received through said fifth communications channel.

15. The apparatus of claim 14 further characterized in that the instrument controller is operative to extract one or more features from one or more captured images, and in response to one or more extracted features said instrument controller is operative to control at least one of the group consisting of said sample imaging means, said shutter actuation means, said first ion beam intensity control means, said first ion beam tilt control means, and said rotation drive.

16. The apparatus of claim 15 further characterized in that the instrument controller is operative to extract a feature from one or more captured images that indicates that said sample is perforated, said instrument controller being further characterized as being operative to respond to the extraction of said feature by causing said first ion beam intensity control means to change the ion beam intensity.

17. The apparatus of claim 15 further characterized in that the instrument controller is operative to extract a feature from one or more captured images that represents a stopping condition, and in response to extracting said stopping condition said instrument controller is operative to cease preparing said sample in said first ion beam.

18. The apparatus of claim 15 further characterized in that the instrument controller is operative to extract a feature from one or more captured images that indicates that said sample is approaching perforation, said instrument controller being further characterized as being operative to respond to the extraction of said feature by causing said first ion beam intensity control means to change the intensity of said first ion beam.

19. The apparatus of claim 15 further characterized in that the instrument controller is operative to: extract a feature from one or more captured images that is representative of one or more interference rings; and extract a feature from one or more captured images that is representative of a change over time of said one or more interference rings; said instrument controller being further characterized as being operative to respond to the extraction of said features by causing said first ion beam intensity control means to change the intensity of said first ion beam.

20. The apparatus of claim 14 further characterized in that the rotation drive is operative to provide a rotation angle to the instrument controller, and the instrument controller is operative to capture an image and annotate said captured image with said rotation angle.

21. The apparatus of claim 14 further characterized in that the rotation drive is operative to provide a rotation angle to the instrument controller, and the instrument controller is operative to capture one or more images at substantially the same rotation angle.

22. The apparatus of claim 21 further characterized in that the instrument controller is operative to use one or more acquisition parameters to control at least one from the group consisting of said sample imaging means, said shutter actuation means, said first ion beam intensity control means, and said first ion beam tilt control means; and said rotation drive, when said shutter means is in said shutter closed position, and the apparatus is further characterized in that the instrument controller is operative to use one or more acquisition parameters to control at least one of the group consisting of said sample imaging means, said shutter actuation means, said first ion beam intensity control means, said first ion beam tilt control means, and said rotation drive, when said shutter means is in said shutter open position.

* * * * *